US00PP17361P2

(12) United States Plant Patent
Egger

(10) Patent No.: US PP17,361 P2
(45) Date of Patent: Jan. 16, 2007

(54) ***PODOPHYLLUM* PLANT NAMED 'SPOTTY DOTTY'**

(50) Latin Name: *Podophyllum hybrid×Podophyllum delavayi*
Varietal Denomination: Spotty Dotty

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 66 days.

(21) Appl. No.: 11/172,134

(22) Filed: Jun. 29, 2005

(51) Int. Cl.
*A01H 5/00* (2006.01)

(52) U.S. Cl. ..... Plt./373; Plt./263

(58) Field of Classification Search ..... None
See application file for complete search history.

(56) References Cited

PUBLICATIONS http://www.plantdelights.com/Catalog/current/Detail/06301.html *Podophyllum* 'Spotty Dotty' PPAF, PVR Apr. 11, 2006*

* cited by examiner

*Primary Examiner*—Wendy Haas
(74) *Attorney, Agent, or Firm*—Klarquist Sparkman, LLP

(57) ABSTRACT

A new and distinct *Podophyllum* plant characterized by beautiful large umbrella-shaped, lobed leaves with an attractive brown-spotted spring color followed by green leaves with lighter spots and larger maroon red flowers in clusters.

2 Drawing Sheets

Botanical denomination: *Podophyllum* hybrid (*Podophyllum* hybrid×*Podophyllum delavayi*).

Variety designation: 'Spotty Dotty'.

The present invention relates to a new and distinct cultivar of *Podophyllum* hybrid and given the cultivar name 'Spotty Dotty'. *Podophyllum* is in the family Berberidaceae.

This new cultivar originated from a cross between *Podophyllum* hybrid '374' (an unpatented proprietary plant) as the seed parent and *Podophyllum delavayi* '64' (an unpatented proprietary plant) as the pollen parent. The seed parent, *Podophyllum* hybrid '374', is an outstanding selection out of a hybrid swarm from a Japanese nursery, which is believed to have come from *P. difforme, P. delavayi*, and *P. versipelle*. The pollen parent, *Podophyllum delavayi* '64' is a highly colored selection. The new cultivar was chosen for its outstanding foliage and vigor.

This plant is characterized by the following:

1. Beautiful large umbrella shaped, lobed leaves with an attractive brown spotted spring color followed by green leaves with lighter spots.
2. Two leaves per crown that will increase in size with maturity to 40 cm. or more wide.
3. Numerous large red maroon flowers with maturity.
4. A rhizomatous habit.
5. Excellent vigor.

This new cultivar has been reproduced only by asexual propagation (tissue culture). Each of the progeny exhibits identical characteristics to the original plant. Asexual propagation by tissue culture using standard micropropagation techniques with side shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
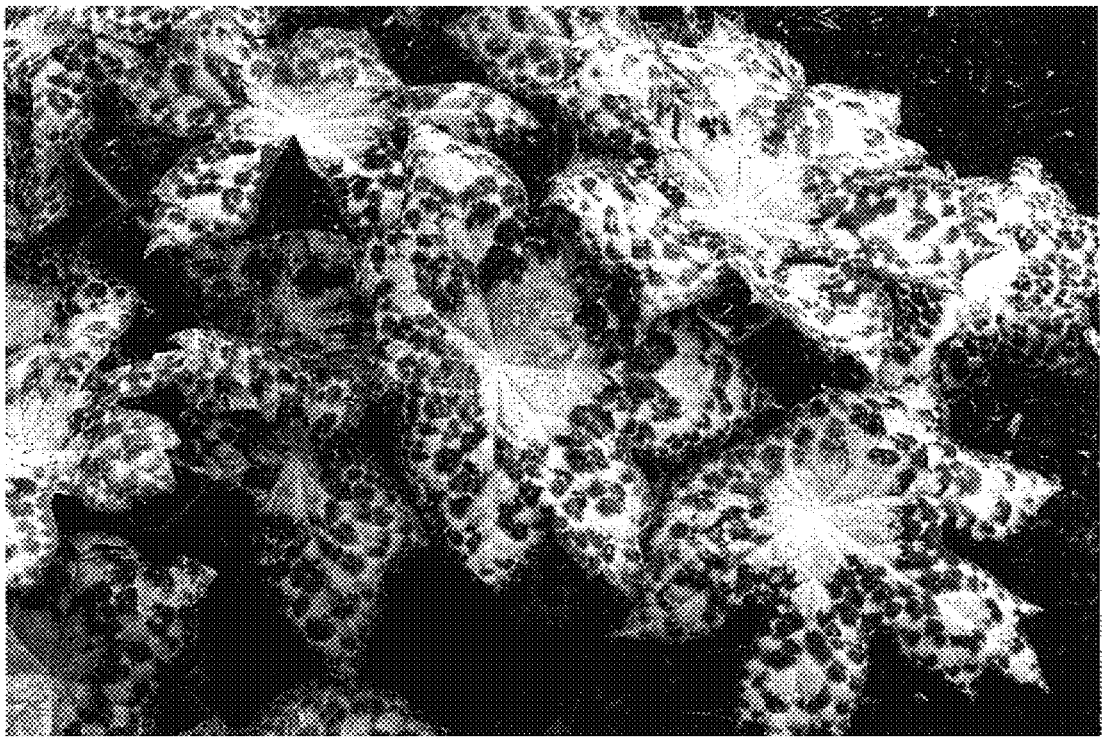
FIG. 1 shows a three-year-old *Podophyllum* 'Spotty Dotty' in the spring in full color growing in the ground in the shade house.
Figure 2:
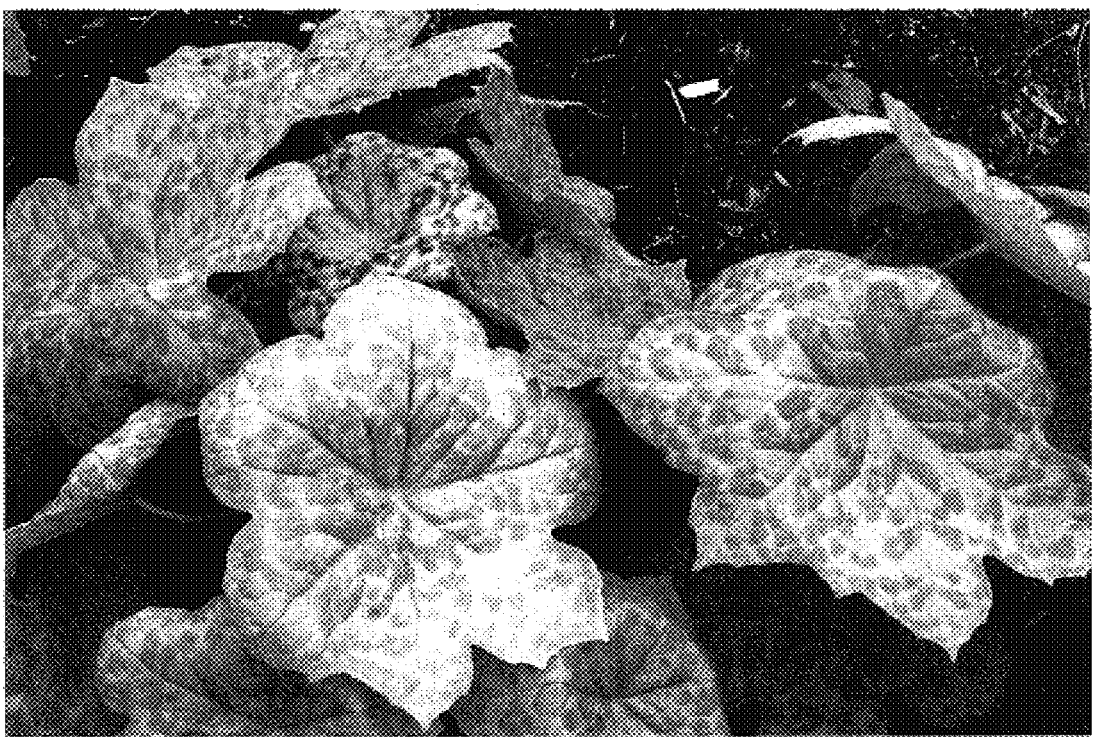
FIG. 2 shows a close up of the flowers.
Figure 3:
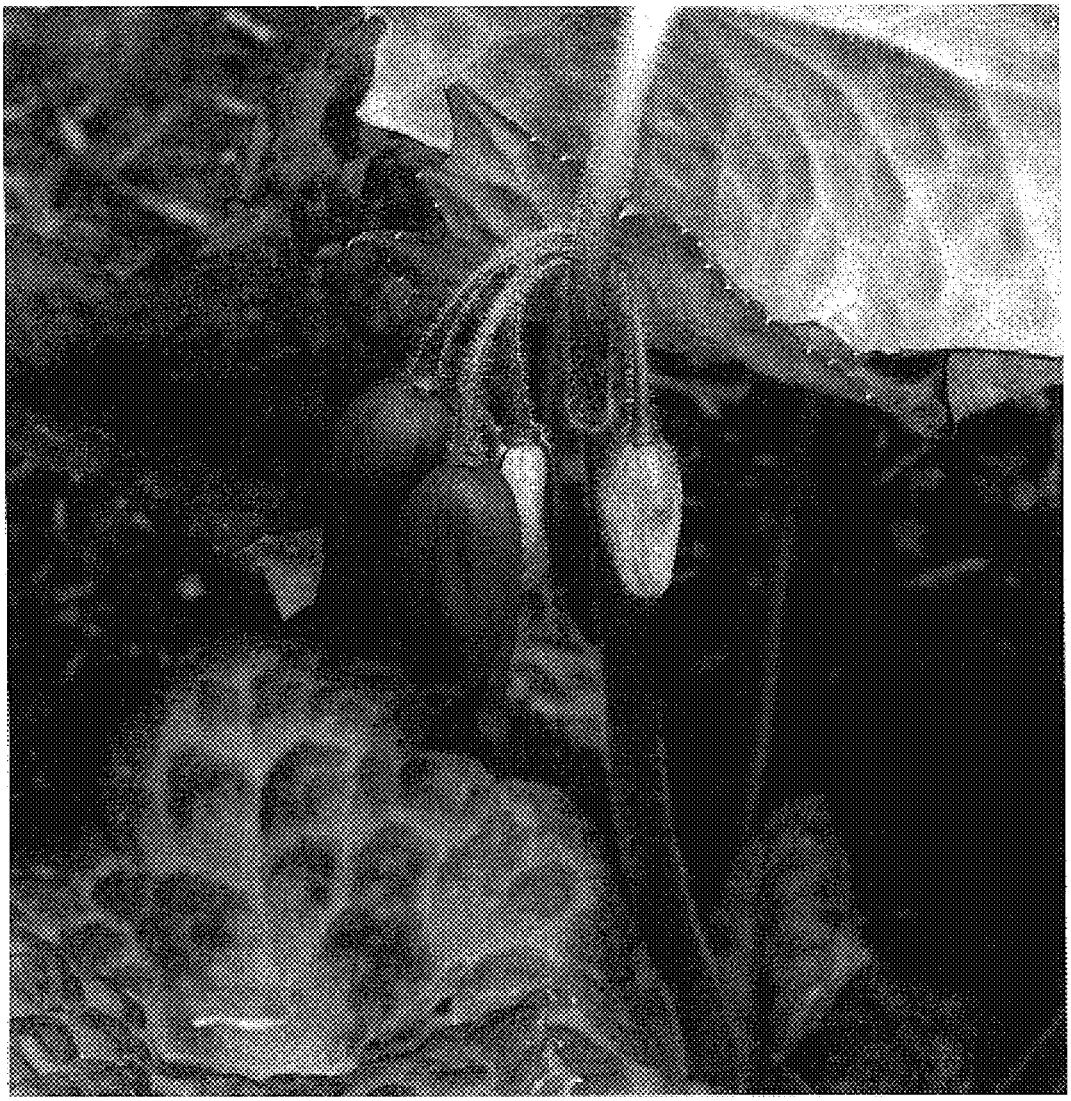
FIG. 3 shows the same plant in the summer.

The following is a detailed description of the new *Podophyllum* cultivar based on observations of three-year-old specimens grown in the ground in an open air shade house with 50% shade cover and added irrigation in the summer months in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Plant:

*Type.*—Herbaceous perennial.

*Form.*—Stoutly rhizomatous, with two leaves per crown when mature and flowering. Juvenile crowns have one leaf per crown and no flowers.

*Hardiness.*—U.S.D.A. Hardiness Zones 6–9.

*Size.*—60 cm tall and 90 cm wide with 5 crowns.

Stem:

*Type.*—Perennial with annual erect aerial stems (stalk between the rhizome and the lamina) with one leaf per stem on young crowns to a maximum of two leaves per crown.

*Size.*—Grows to 33 cm tall and 9 mm wide.

*Surface texture.*—Pubescent, with many long soft hairs.

*Color.*—Closest to Greyed Red 182B.

Leaf:

*Type.*—Simple.

*Arrangement.*—Alternate.

*Shape.*—Peltate, petiole attached off center.

*Blade size.*—22 to 28 cm wide on mature leaves, grows to 37 cm wide on juvenile leaf.

*Venation.*—Palmate with 6 to 7 main lobes.

*Margins.*—Palmatifid, slightly revolute and irregularly and coarsely serrate, each tooth with a prominent mucro.

*Lobing.*—6 lobes, mature leaves with deeper lobes, the four lobes on the outside of the petiole are ovate in shape and distinct, the two on the inside are connected in the middle.

*Apices.*—Mucronulate.

*Base.*—Leaf dips in where connected to petiole.

*Texture.*—Leathery.

*Surface texture.*—Glabrous on top and pubescent on bottom.

*Petiole.*—(Stalk between the aerial stem and the lamina). Length — 10 to 16 cm for terminal leaf and 8 to 16 cm for lower leaf. Width — 3 mm. Vestiture — Pubescent with many long soft hairs. Color — Greyed Red 182A.

*Leaf color.*—Varies with light, temperature and age. Best leaf color occurs with bright shade, cool temperatures and new leaves. Abaxial — New spring leaves are chartreuse, Yellow Green 145C, with brown spots, Brown 200B and brownish edges, Greyed Orange 176A and B. Summer leaves have no brown, Yellow Green 145C with spots of Yellow Green 146A. Adaxial — Yellow Green 147C.

Inflorescence: Borne on the petiole below the base of the terminal leaf.

*Number and type.*—4 to 7 in an umbel-like group, pendulous.

*Size.*—10 cm wide and 12 cm deep including pedicels.

*Pedicel.*—Length — 5.3 cm. Surface texture — Grey Brown 199B with some maroon, Greyed Purple 187A.

*Bloom time.*—Spring, May in Canby, Oreg.

Flower bud:

*Size.*—1.5 cm wide and 3 cm deep.

*Description.*—Upside down teardrop shape.

*Color.*—Tan, Greyed Purple 183D and Grey Brown 199C.

Flower:

*Type.*—Actinomorphic, bisexual, and pendulous.

*Size.*—3 cm. wide and 8 cm. deep.

*Color.*—Deep red-purple, Greyed Purple 187B but brighter and more purple.

*Petal number.*—6.

*Petal size.*—1.2 cm. wide and 8.5 cm. deep.

*Petal shape.*—Lanceolate with a rounded irregular apex, slight twist at the ends, margins entire.

*Petal surface texture.*—Glabrous on both sides.

*Calyx.*—Fugacious, cupped. Sepal number — 5 to 6. Size — 1 to 1.3 cm wide and 2.5 to 3.33 cm deep. Surface texture — Pubescent on the outside, glabrous inside. Color — Greyed Red 180A.

*Stamens.*—Number — 6. Size — 3 cm long and 3 mm wide. Filaments — 7 mm long and 1.5 mm wide, color is Greyed Purple 187B. Anthers — Oblong with tip curling. Between Yellow Green 152D and Greyed Yellow 160A before dehiscence. Anther mucro is 4 mm long. Pollen — Greyed Yellow 160B.

*Pistil.*—1.8 cm long, Yellow Green 152A.

*Stigma.*—Oval from top (4 mm by 7 mm), convoluted, Yellow White 159A on edges and Greyed Red 180A below.

*Fragrance.*—Heavy, slightly unpleasant.

Fruit:

*Type.*—Spherical, fleshy berry.

*Fertility.*—Self-incompatible, should outcross.

*Color.*—Green 138A, when mature, and glaucous.

Seed:

*Shape.*—Oval.

*Size.*—3 mm long.

*Color.*—Tan, Yellow White 158A.

Pests and diseases: *Podophyllum*, when grown in moist, well-drained, humus rich soil in the shade, have very few pest problems. The species is usually susceptible to root rots in poorly drained soils. No problems observed on plants grown commercially in Canby, Oreg.

COMPARISONS

This new cultivar was selected and compared to the less colored and unpatented proprietary parent plants. The parent plants were selected from a large population of well-marked plants. *Podophyllum* 'Spotty Dotty' has been shown to have much superior leaf markings and colorings.

I claim:

1. A new and distinct variety of *Podophyllum* plant as herein illustrated and described.

* * * * *